United States Patent
Perfitt et al.

(10) Patent No.: US 9,801,793 B2
(45) Date of Patent: Oct. 31, 2017

(54) DRY SHAMPOO COMPOSITION

(71) Applicant: Herb UK Limited, Lymington, Hampshire (GB)

(72) Inventors: Raoul John Perfitt, Lymington (GB); Cicely Andrea Ruth Carimbocas, Lymington (GB)

(73) Assignee: HERB UK LIMITED, Lymington (GB)

( * ) Notice: Subject to any disclaimer, the term of this patent is extended or adjusted under 35 U.S.C. 154(b) by 0 days.

(21) Appl. No.: 15/083,952

(22) Filed: Mar. 29, 2016

(65) Prior Publication Data

US 2016/0317396 A1    Nov. 3, 2016

(30) Foreign Application Priority Data

Apr. 29, 2015   (GB) .................................. 1507313.3

(51) Int. Cl.
| | | |
|---|---|---|
| *A61K 8/02* | (2006.01) | |
| *A61Q 13/00* | (2006.01) | |
| *A61K 8/36* | (2006.01) | |
| *A45D 19/02* | (2006.01) | |
| *A61K 8/25* | (2006.01) | |
| *A61K 8/26* | (2006.01) | |
| *A61Q 5/02* | (2006.01) | |
| *A61K 8/97* | (2017.01) | |
| *A61K 8/73* | (2006.01) | |
| *A45D 19/00* | (2006.01) | |

(52) U.S. Cl.
CPC .............. *A61K 8/022* (2013.01); *A45D 19/02* (2013.01); *A61K 8/0241* (2013.01); *A61K 8/25* (2013.01); *A61K 8/26* (2013.01); *A61K 8/36* (2013.01); *A61K 8/732* (2013.01); *A61K 8/97* (2013.01); *A61Q 5/02* (2013.01); *A61Q 13/00* (2013.01); *A45D 2019/005* (2013.01); *A45D 2019/0033* (2013.01); *A61K 2800/31* (2013.01); *A61K 2800/524* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,407,789 A | 10/1983 | Eigen et al. | |
| 2003/0138533 A1* | 7/2003 | Simmons | A23L 3/3463 426/321 |
| 2006/0093691 A1* | 5/2006 | Thurot | A61K 8/02 424/776 |
| 2012/0282190 A1* | 11/2012 | Hammer | A61K 8/046 424/47 |
| 2014/0000643 A1 | 1/2014 | Swaile et al. | |
| 2014/0193500 A1* | 7/2014 | Cotrell | A61K 8/84 424/489 |
| 2016/0287484 A1 | 10/2016 | Neame | |

FOREIGN PATENT DOCUMENTS

| | | | | |
|---|---|---|---|---|
| EP | 2777770 A1 | | 9/2014 | |
| FR | 2721507 A1 | | 12/1995 | |
| GB | 2520436 | * | 5/2015 | .............. A61K 8/60 |
| WO | 2008016701 A2 | | 2/2008 | |
| WO | 2011056625 A1 | | 5/2011 | |
| WO | 2013143792 A2 | | 10/2013 | |

OTHER PUBLICATIONS

International Search Report and Written Opinion dated Jun. 14, 2016 in International Patent Application No. PCT/GB2016/050777, 68 pages.
Search Report dated Jan. 27, 2016 in priority application No. GB 1507313.3, 2 pages.
Tints of Nature, "Dry Shampoo", available via URL: https://web.archive.org/web/20150411051702/http://www.tintsofnature.com/homepage-offers/dry-shampoo [Archived date Apr. 11, 2015].

\* cited by examiner

*Primary Examiner* — Bethany Barham
*Assistant Examiner* — Barbara Frazier
(74) *Attorney, Agent, or Firm* — Perkins Coie LLP

(57) ABSTRACT

The present technology provides a dry shampoo composition comprising clay, natural starches and a natural oil absorbent. Such dry shampoo compositions are highly absorbent, fine, light and resistant to clumping. In some embodiments, the dry shampoo compositions are useful as alternatives to conventional wet shampoo in methods for cleaning hair.

10 Claims, No Drawings

DRY SHAMPOO COMPOSITION

CROSS-REFERENCE TO RELATED APPLICATIONS

This application claims priority to GB 1507313.3, filed 29 Apr. 2015, which is incorporated herein by reference in its entirety.

TECHNICAL FIELD

The present technology relates to a dry shampoo composition. In particular, the present technology relates to a dry shampoo composition containing Oryza sativa (Rice) hull powder and a smectite clay together with a specific combination of natural starches.

BACKGROUND

The practice of regularly washing head hair has become ubiquitous in modern society. Frequently, the hair is washed using a conventional liquid or gel shampoo, which is applied to the hair and then rinsed out with water. However, dry shampoos, which do not require the use of water, are becoming increasingly popular. The use of a dry shampoo can save time and provide added convenience since no rinsing with water is needed; rather, removal of the dry shampoo can be effected simply by brushing or blotting it from the scalp. Furthermore, it has been suggested that excessively frequent wet-washing can be associated with damage to the hair, particularly for those with fine hair. The use of dry shampoos may therefore provide an alternative or complementary method for maintaining the cleanliness and appearance of the hair without incurring the damaging effects of excessive washing in water.

However, dry shampoos currently on the market can have various disadvantageous characteristics. Some such shampoos contain a number of synthetic components such as, for example, bulking agents, which can be undesirable both from a customer perception perspective and from an environmental viewpoint. Dry shampoo powders may also have unsatisfactory capacity to absorb oil, have a heavy feel or a tendency to form clumps of particles (which can both reduce the effectiveness of the product and give rise to unsightly residues in the hair). Still further, when the intended use is for a subject with dark hair, it has often been considered necessary for the dry shampoo powders additionally to incorporate pigments to avoid leaving unattractive and obviously visible light-coloured remnants of material in the hair after cleaning. There is therefore a need for new dry shampoo compositions for use as an alternative to conventional wet shampoo and dry shampoo products.

DETAILED DESCRIPTION

The present technology is related generally to dry shampoo compositions. In one embodiment of the present technology, for example, a dry shampoo composition incorporates substantially or exclusively natural ingredients. Such dry shampoo compositions are expected to be fine, light and highly absorbent, and is suitable for cleaning dark hair without the need to incorporate additional colorant materials.

According to one aspect, for example, the present technology provides a dry shampoo composition comprising: 0.5 to 5 wt % of Oryza sativa (Rice) hull powder; 1 to 10 wt % of a smectite clay; 30 to 60 wt % of tapioca starch; 30 to 60 wt % of corn starch; and 3 to 20 wt % of potato starch.

According to another aspect, the present technology provides a product comprising a dry shampoo composition of the present technology and a spray bottle adapted to deliver the dry shampoo composition as a powder spray.

In another aspect, the present technology provides a method of cleaning the hair, which comprises applying a dry shampoo composition of the present technology to the hair.

Where indicated herein, the components of the dry shampoo compositions according to the present technology are identified by reference to their INCI names. INCI (International Nomenclature of Cosmetic Ingredients) is an international designation for the declaration of the ingredients on the packaging of cosmetics. INCI names are specific and uniform scientific names which are neither trade names nor common names.

One component of a dry shampoo composition of the present technology is Oryza sativa (Rice) hull powder (which is an INCI name). Oryza sativa (Rice) hull powder is commercially available from Soliance (Pomade France) and is referred to interchangeably herein as rice silk. Oryza sativa (Rice) hull powder is a natural product that is obtained from the hull surrounding rice grains. It is an ultra-fine, natural powder capable of matifying skin and hair by absorbing excess sebum. It has been found to impart a silky, smooth feel to compositions of the present technology, and may improve the manageability of hair. It has an exceptionally high oil absorption capacity (e.g., greater than 300%). The Oryza sativa (Rice) hull powder is preferably present in a dry shampoo composition of the present technology in an amount of 0.5 to 2 wt %, more preferably still 0.75 to 1.5 wt %.

Another component of a composition according to the present technology is a smectite clay. Smectite clays are a group of clay minerals that are able to adsorb water. In compositions of the present technology, the smectite clay has been found to help the powder flow and to prevent it from clumping. It is a non-abrasive material and typically is a soft, white powder.

In some embodiments, a composition according to the present technology comprises hectorite (which is an INCI name) as a smectite clay. The smectite clay may be present in a dry shampoo composition according to the present technology in an amount of 1 to 4 wt %, such as 1.5 to 2.5 wt %.

In some embodiments, a composition according to the present technology comprises tapioca starch (which is an INCI name). Tapioca starch is a product that is naturally derived from cassava root. It is a velvety, soft after-feel cleanser, which absorbs oil, reduces greasiness and cleans the hair. It has been found that it also imparts softness and smoothness to finished dry shampoo compositions of the present technology. In some embodiments, tapioca starch is present in a dry shampoo composition of the present technology in an amount of 37 to 53 wt %, such as 40 to 50 wt %.

In some embodiments, a composition according to the present technology comprises corn starch. Corn starch, also known as maize starch, is an unmodified, natural starch that is extracted from corn kernels. It is a natural, biodegradable, sustainable and non-irritating substance. It possesses anti-inflammatory properties and is capable of soothing itchy skin and scalp. When incorporated into compositions according to the present technology, corn starch has been found to provide a unique powdery-dry, smooth after-feel, to control immediate and residual shine and oiliness, and to reduce any perceivable tackiness and stickiness.

In some embodiments, the corn starch is *Zea Mays* (Corn) Starch (which is an INCI name). *Zea Mays* (Corn) Starch is obtained from the corn *Zea mays* L., Gramineae. In some embodiments, corn starch is present in a dry shampoo composition of the present technology in an amount of 37 to 53 wt %, such as 40 to 50 wt %.

In some embodiments, a composition according to the present technology comprises potato starch. Potato starch is a starch that is extracted from potatoes and it is thus another natural product. When incorporated into a composition of the present technology, the potato starch has been found to enhance hair combing manageability, generate a clean and fresh feel, leave the hair feeling soft and conditioned, and leave the hair looking smooth and silky.

In some embodiments, the potato starch is *Solanum Tuberosum* (Potato) starch (which is an INCI name). In some embodiments, the potato starch is present in a dry shampoo composition of the present invention in an amount of 3 to 10 wt %, for example 5 to 8 wt %.

In some embodiments, a composition according to the present technology further comprises at least one preservative. In some embodiments, the at least one preservative is potassium sorbate, which is a white crystalline powder with strong antimicrobial properties. Other suitable preservatives include salicylic acid, sodium sulphite, sodium benzoate and benzoic acid.

If present, the at least one preservative is present in a dry shampoo composition according to the present technology in an amount of not more than 3 wt %, for example in an amount of not more than 2 wt %, or in an amount of 0.1 to 2 wt % (wherein all of these amounts refer to the total content of the at least one preservative).

In some embodiments, a composition according to the present technology comprises at least one fragrance. The incorporation of fragrances in cosmetic products such as shampoos is well established and those of skill in the art would routinely be able to select a suitable fragrance or combination of fragrances to achieve the desired odour. In some embodiments, the at least one fragrance comprises, consists essentially of, or consists of natural fragrances, i.e. fragrant compounds that are derived from natural sources rather than being synthetically produced. Examples of suitable fragrances include limonene, linalool and eugenol (all of which are INCI names).

If present, the at least one fragrance is present in a dry shampoo composition according to the present technology in an amount of not more than 1 wt %, for example in an amount of not more than 0.5 wt % or in an amount of 0.05 to 0.5 wt % (wherein all of these amounts refer to the total content of the at least one fragrance).

In some embodiments, a composition according to the present technology comprises, consists essentially of, or consists of:
0.5 to 2 wt % of *Oryza sativa* (Rice) hull powder;
1 to 4 wt % of a smectite clay, such as hectorite;
37 to 53 wt % of tapioca starch;
37 to 53 wt % of corn starch;
3 to 10 wt % of potato starch;
not more than 2 wt % of at least one preservative; and
not more than 0.5 wt % of at least one fragrance.

In some embodiments, a composition according to the present technology comprises, consists essentially of, or consists of:
about 1 wt % of *Oryza sativa* (Rice) hull powder;
about 2 wt % of a smectite clay (preferably hectorite);
about 45 wt % of tapioca starch;
about 45 wt % of corn starch;
about 6.3 wt % of potato starch;
about 0.5 wt % of at least one preservative; and
about 0.2 wt % of at least one fragrance.

In some embodiments, "about" means plus or minus ten percent of the specified amount. For example, about 1 wt % means 0.9 to 1.1 wt % (plus or minus ten percent, namely 0.1, of 1).

In some embodiments, a dry shampoo composition according to the present technology is a dry powder. In some embodiments, a dry shampoo composition according to the present technology contains at most 1 wt % of water, such as no more than 0.5 wt %, less than 0.1 wt %, or substantially 0 wt % or 0 wt % of water. In some embodiments, a dry shampoo composition according to the present technology contains at most 1 wt %, in total, of any liquid substance, such as no more than 0.5 wt %, in total, of any liquid substance, less than 0.1 wt %, in total, of any liquid substance, or substantially 0 wt % or 0 wt %, in total, of any liquid substance. In some embodiments, a dry shampoo composition according to the present technology does not comprise an aerosol propellant.

In some embodiments, a dry shampoo composition according to the present technology includes no more than 1 wt %, no more than 0.1 wt %, or 0 wt % of any synthetic or partially synthetic bulking agent, for example aluminium starch octenylsuccinate (which is an INCI name).

In some embodiments, a dry shampoo composition according to the present technology includes no more than 1 wt %, no more than 0.1 wt %, or 0 wt % of either silica or talc, which are bulking agents commonly used in other cosmetic products.

In some embodiments, a dry shampoo composition according to the present technology does not contain a pigment (also referred to herein as a colorant).

In some embodiments, a dry shampoo composition according to the present technology contains not more 5 wt %, no more than 2 wt %, not more than 1 wt %, or substantially 0 wt % or 0 wt %, in total of components other than the *Oryza sativa* (Rice) hull powder, smectite clay, tapioca starch, corn starch, potato starch, (optional) at least one preservative and (optional) at least one fragrance. In some embodiments, a dry shampoo composition according to the present technology contains not more 5 wt %, no more than 2 wt %, or not more than 1 wt %, in total of components other than the *Oryza sativa* (Rice) hull powder, smectite clay, tapioca starch, corn starch and potato starch.

It has surprisingly been found that the specified combination of ingredients, in the specified relative amounts, gives rise to dry shampoo compositions that have particularly advantageous properties. These properties include high absorbency (e.g., of oil/grease that builds up in the hair and which motivates cleaning it), fineness, lightness, and resistance to clumping. By contrast, other dry shampoo compositions tested by the present inventors and which incorporated different components, for example different combinations of starches, were found to have inferior performances with regard to at least one of these characteristics. Additional details may be found in the specific Example disclosed herein.

Furthermore, dry shampoo compositions according to the present technology consist at least substantially of natural components, such as natural starches, rice silk, and naturally occurring smectite clay. Accordingly, dry shampoo compositions according to the present technology consist almost exclusively of natural ingredients, which is beneficial both from an environmental perspective and in view of the increasing sensitivity of consumers to cosmetic compositions that incorporate synthetic ingredients.

Dry shampoo compositions according to the present technology can readily be used to clean the hair of subjects who have any hair colour. For example, dry shampoo compositions according to the present technology can be used to clean the hair of subjects who have dark hair, without leaving unsightly traces of light-coloured material in the hair after use. Without wishing to be bound by theory, this may be due to the fineness, lightness and resistance to clumping of the dry powder compositions disclosed herein. Accordingly there is advantageously no need to incorporate a pigment in the composition when it is formulated for use with dark hair. This is in contrast to some previously known dry shampoo compositions, where it has been necessary to prepare a range of commercial products incorporating pigments adapted for different hair colours.

A still further advantage of dry shampoo compositions according to the present technology is that a relatively small weight of the composition (e.g., on the order of 15 grams) is sufficient to clean the hair a large number of times (e.g., on the order of 100 or more times). Thus a commercial product incorporating a dry shampoo composition of the present technology is suitable for cleaning the hair many more times than would be a conventional wet shampoo product of equivalent weight.

Dry shampoo compositions according to the present technology can advantageously be formulated in a spray bottle, such as a spray bottle for delivering the dry shampoo composition as a powder spray. In some embodiments, the bottle is capable of delivering the dry shampoo composition as a non-aerosol powder spray. Thus, in some embodiments, the product that comprises the dry shampoo composition and the spray bottle does not comprise an aerosol propellant.

The spray bottle may comprise a directional nozzle (e.g., a nozzle that extends away from the main body of the bottle, such as a nozzle that extends away from a cylindrical bottle body). For example, the directional nozzle may extend in a substantially perpendicular direction away from the axis of a cylindrical bottle body. The directional nozzle assists in ensuring that the dry shampoo composition can be effectively delivered to the desired site on the surface of the subject's head, i.e. it allows for easy and thorough access to the scalp and hair. An example of an exemplary spray bottle design is shown in CN 202697535, the content of which is herein incorporated by reference in its entirety. In some embodiments, the spray bottle is not an aerosol bottle.

The present technology also provides a method of cleaning the hair, the method comprising applying a dry shampoo composition as disclosed herein to hair. The method may further comprise removing (e.g., by brushing or blotting) the dry shampoo composition from the hair. In between the steps of applying the dry shampoo composition to the hair and removing it from the hair, the method may further comprise one or both of the following steps: (i) after application, leaving the dry shampoo composition on the hair for a period of time, for example from 20 seconds to 5 minutes, such as from 30 seconds to 2 minutes or for about 1 minute; and (ii) massaging the dry shampoo composition into the scalp (for example, by running fingers through the hair).

If the dry shampoo composition is contained within a spray bottle, it may be preferable to shake the bottle before use. Optionally clothing can be protected before spraying, i.e. before applying the composition of the present technology to the hair.

It may be beneficial to apply the composition to the hair in a stepwise fashion, namely by parting the hair in sections and applying the composition to each section in turn.

Additional aspects of the present technology are illustrated by the following example.

EXAMPLE

A variety of dry shampoo compositions were prepared containing the components set out in Table 1. Ex 1 to Ex 3 shows representative dry shampoo compositions of the present technology, while C1 to C13 are a range of comparative compositions.

In this table, all amounts are expressed in % w/w. Amaze XT™ is dehydroxanthan gum (INCI name), which is commercially available from AkzoNobel™ (Amsterdam, The Netherlands) as an off-white powder. PVP is polyvinylpyrrolidone.

TABLE 1

| Component | Composition | | | | | | | |
|---|---|---|---|---|---|---|---|---|
| | Ex 1 | Ex 2 | Ex 3 | C1 | C2 | C3 | C4 | C5 |
| Rice silk | 1 | 1 | 1 | 1 | | | 1 | 1 |
| Clay | $2^a$ | $2^a$ | $2^a$ | | $2^{b1}$ | $5^{b2}$ | $2^{b1}$ | $2^{b1}$ |
| Tapioca starch | 45 | 40 | 45 | | | | | |
| Corn starch | $45^a$ | $47.5^c$ | $45^d$ | $93.1^c$ | $47.6^d$ | $59.4^d$ | $31.4^d$ | $65^c$ |
| Potato starch | 6.3 | 10 | 7.5 | | 47.8 | 30 | 60 | 31.4 |
| Rice starch | | | | | | | | |
| Oat kernel flour | | | | | | | 5 | 5 |
| Amaze XT ™ | | | | 5 | 2 | | | |
| PVP | | | | | | | | |
| Aloe | | | | 0.3 | | | | |
| Potassium sorbate | 0.5 | 0.5 | 0.5 | 0.6 | 0.6 | 0.6 | 0.6 | 0.6 |
| Fragrances | 0.2 | | | | | | | |

| Component | Composition | | | | | | | |
|---|---|---|---|---|---|---|---|---|
| | C6 | C7 | C8 | C9 | C10 | C11 | C12 | C13 |
| Rice silk | 2 | 1 | 1 | | | | | |
| Clay | $10^a$ | $2^a$ | $2^a$ | $2^a$ | $4.5^a$ | $10^{b1}$ | $4^a$ | $4^a$ |
| Tapioca starch | | | | 47.5 | 30 | 10 | 45 | 25 |
| Corn starch | $67.4^c$ | $80^c$ | $80^d$ | $50^c$ | $30^c$ | $29.5^c$ | $34.5^c$ | $20^c$ |
| Potato starch | 20 | 16.4 | 16.4 | | | | | |

TABLE 1-continued

| | | | | | | | | |
|---|---|---|---|---|---|---|---|---|
| Rice starch | | | | | 35 | 50 | 15 | 47.5 |
| Oat kernel flour | | | | | | | | |
| Amaze XT ™ | | | | | | | | |
| PVP | | | | | | | 1 | 3 |
| Aloe | | | | | | | | |
| Potassium sorbate | 0.6 | 0.6 | 0.6 | 0.5 | 0.5 | 0.5 | 0.5 | 0.5 |
| Fragrances | | | | | | | | |

<sup>a</sup>Hectorite (INCI name);
<sup>b1</sup>Kaolin (INCI name), a white kaolinite clay;
<sup>b2</sup>Kaolin (INCI name), a brown kaolinite clay
<sup>c</sup>Corn starch from AkzoNobel ™ (Purity 21C starch ™);
<sup>d</sup>Corn starch from Roquette ™.

Compositions were tested by a panel of in-house testers, who assessed them for factors such as absorbency, fineness, lightness, and resistance to clumping. It was considered that the composition of Ex 1 achieved a good combination of these properties. The compositions of C1 to C13 were considered however to have inferior properties.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments applicable to a wide range of compositions.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A product comprising a dry shampoo composition and a spray bottle for delivering the dry shampoo composition as a powder spray, wherein the dry shampoo composition comprises:

0.5 to 5 wt % of *Oryza sativa* (Rice) hull powder;
1.5 to 2.5 wt % of a smectite clay;
30 to 56 wt % of tapioca starch;
37 to 53 wt % of corn starch; and
5 to 8 wt % of potato starch.

2. The product according to claim 1 wherein the smectite clay is hectorite.

3. The product according to claim 1 wherein the dry shampoo composition comprises 0.5 to 2 wt % of the *Oryza sativa* (Rice) hull powder.

4. The product according to claim 1 wherein the dry shampoo composition comprises 37 to 53 wt % of the tapioca starch.

5. The product according to claim 1 wherein the dry shampoo composition further comprises at least one preservative.

6. The product according to claim 5 wherein the at least one preservative is present in the dry shampoo composition in a total amount of not more than 2 wt %.

7. The product according to claim 5 wherein the at least one preservative comprises potassium sorbate.

8. The product according to claim 1 wherein the dry shampoo composition further comprises at least one fragrance.

9. The product according to claim 8 wherein the at least one fragrance is present in the dry shampoo composition in a total amount of not more than 0.5 wt %.

10. The product according to claim 1 wherein the dry shampoo composition contains not more than 5 wt % in total of components other than the *Oryza sativa* (Rice) hull powder, the smectite clay, the tapioca starch, the corn starch and the potato starch.

* * * * *